(12) United States Patent
Ogawa (10) Patent No.: US 7,715,700 B2
(45) Date of Patent: May 11, 2010

(54) METHOD, DEVICE, AND BAG FOR WARMING INFUSION LIQUID

(76) Inventor: Genshirou Ogawa, 111-2, Aza-Nishikoken, Oaza-Inuyama, Inuyama-shi, Aichi-ken (JP) 484-0081

( * ) Notice: Subject to any disclaimer, the term of this patent is extended or adjusted under 35 U.S.C. 154(b) by 638 days.

(21) Appl. No.: 10/588,817

(22) PCT Filed: Feb. 17, 2004

(86) PCT No.: PCT/JP2004/001749

§ 371 (c)(1),
(2), (4) Date: Apr. 17, 2007

(87) PCT Pub. No.: WO2005/077436

PCT Pub. Date: Aug. 25, 2008

(65) Prior Publication Data

US 2008/0039815 A1    Feb. 14, 2008

(51) Int. Cl.
*A61F 7/00* (2006.01)
(52) U.S. Cl. .................. 392/470; 392/479; 604/113
(58) Field of Classification Search ............ None
See application file for complete search history.

(56) References Cited

U.S. PATENT DOCUMENTS

| | | | |
|---|---|---|---|
| 3,485,245 A * | 12/1969 | Terwilliger et al. | 604/114 |
| 3,612,059 A * | 10/1971 | Ersek | 607/106 |
| 4,077,390 A | 3/1978 | Stanley et al. | |
| 4,293,762 A * | 10/1981 | Ogawa | 392/470 |
| 4,672,178 A | 6/1987 | Wada et al. | |
| 4,680,445 A * | 7/1987 | Ogawa | 392/470 |
| 4,731,072 A * | 3/1988 | Aid | 604/408 |
| 4,772,778 A | 9/1988 | Ogawa | |
| 4,934,336 A | 6/1990 | White | |
| 5,250,032 A * | 10/1993 | Carter et al. | 604/113 |
| 5,254,094 A * | 10/1993 | Starkey et al. | 604/113 |
| 6,484,514 B1 | 11/2002 | Joseph et al. | |
| 6,788,885 B2 * | 9/2004 | Mitsunaga et al. | 392/470 |
| 7,158,719 B2 * | 1/2007 | Cassidy | 392/494 |

FOREIGN PATENT DOCUMENTS

| | | |
|---|---|---|
| DE | 100 43 533 A1 | 3/2002 |
| GB | 2 160 965 A | 1/1986 |
| JP | U-49-101588 | 12/1972 |
| JP | A 62-019163 | 1/1987 |
| JP | A 01-312356 | 12/1989 |
| JP | A-02-234761 | 9/1990 |
| JP | U-02-126652 | 10/1990 |

(Continued)

*Primary Examiner*—Thor S Campbell
(74) *Attorney, Agent, or Firm*—Oliff & Berridge, PLC (57) ABSTRACT

An infusion fluid warming apparatus for warming an infusion fluid to a predetermined temperature prior to supply of the infusion fluid into a living body through an infusion fluid tube. The apparatus includes: (a) a tube holding device detachably holding the infusion tube; and (b) a heat accumulator member generating a latent heat in phase change thereof from liquid phase to solid phase. The heat accumulator member is disposed in the tube holding device, so as to warm the infusion fluid passing through the infusion fluid tube that is held by the tube holding device, by the latent heat generated in the phase change from the liquid phase to the solid phase. Also, disclosed is an infusion fluid warming method.

8 Claims, 5 Drawing Sheets

FOREIGN PATENT DOCUMENTS

| | | |
|---|---|---|
| JP | A-05-237161 | 9/1993 |
| JP | A 07-289579 | 11/1995 |
| JP | A 07-328120 | 12/1995 |
| JP | A-10-005267 | 1/1998 |
| JP | A 10-043295 | 2/1998 |
| JP | A 2000-502938 | 3/2000 |
| JP | A 2001-091175 | 4/2001 |
| JP | A-2002-013893 | 1/2002 |
| JP | A-2002-098455 | 4/2002 |
| JP | A 2002-102349 | 4/2002 |
| WO | WO 00/48646 A2 | 8/2000 |
| WO | WO 02/051482 A1 | 7/2002 |

* cited by examiner

METHOD, DEVICE, AND BAG FOR WARMING INFUSION LIQUID

TECHNICAL FIELD

The present invention relates to an improvement in an infusion fluid warming apparatus for warming each of various kinds of infusion fluids to a suitable temperature prior to supply of the infusion fluid into a living body, for example, in a medical field.

BACKGROUND ART

In a field of medical activity, for example, there is a case where an infusion fluid such as blood, plasma, physiological saline, nutrition fluid and medical fluid is supplied into a living body. In such a case, for example, it is common that the infusion fluid is stored in an infusion fluid container such as bag and bottle that is hung by a stand, and is infused into a blood vessel of the living body through an intravenous drip cylinder, a roller clamp, an infusion fluid tube and a hypodermic needle that are connected to the infusion fluid container, or is supplied directly into a digestive organ of the living body through the infusion fluid tube, or is supplied orally into a mouth of the living body through the infusion fluid tube.

In most cases, the infusion fluid is stored at a relatively low temperature due to request for maintaining the quality, so that the infusion fluid is required to be warmed to about a temperature of the living body as rapidly as possible in a case where rapid supply of the infusion fluid is necessary, for example, in event of an emergency operation. To this end, there has been developed an infusion fluid warming apparatus for warming the infusion fluid to a suitable temperature, during process of rapidly supplying the infusion fluid as described above. Examples of such an infusion fluid warming apparatus are disclosed in Patent Document 1 and Patent Document 2. The infusion fluid warming apparatus disclosed in Patent Document 1 is a bag-shaped heat exchanger pack which has passages for guiding the infusion fluid and a warming medium so that the infusion fluid is warmed by the warming medium. The infusion fluid warming apparatus disclosed in Patent Document 2 has an arrangement in which the fluid is warmed while passing through a seat-like sealed passageway that covers a circumferential surface of a heating core.

[Patent Document 1] JP2002-102349A
[Patent Document 2] JP2000-502938A

However, since each of the above-described conventional infusion fluid warming apparatuses requires a device for circulating the warming medium or the heating core whose temperature is controlled, there is a case where the apparatus can not warm the infusion fluid in an emergency facility in transfer of a patient or in outdoors due to difficulty in obtaining a power source. On the other hand, it might be possible to use, as a source for heating the infusion fluid, a heating element made of a material that generates a heat by its reaction with oxygen contained in an air, or a heating element that generates a heat by reaction of quicklime with water. However, the heating element utilizing such an exothermic reaction does not have a function for rapidly warming the infusion fluid and maintaining the warmed infusion fluid at a constant temperature for a relatively large length of time. Thus, the heating element utilizing the exothermic reaction is unsuitable for warming the infusion fluid.

The present invention was made in the light of the background art discussed above. It is therefore an object of the invention to provide an infusion fluid warming apparatus capable of rapidly warming an infusion fluid even in a circumstance without availability of a power source and maintaining the warmed infusion fluid at a constant temperature for a relatively large length of time.

DISCLOSURE OF INVENTION

The present inventor has made extensive studies for achieving the above-described object, and found out that a material whose melting point is in the vicinity of or higher than a body temperature by a predetermined value rapidly generates a latent heat in phase change of the material, and that a temperature of the generated heat can be rapidly elevated and the elevated temperature can be held substantially constant for a relatively large length of time. That is, the present inventor found out that the material has an extremely excellent characteristic as the source for heating the infusion fluid. The present invention was made on the basis of this finding.

The gist of a method invention as a first invention is that, in an infusion fluid warming method of warming an infusion fluid to a predetermined temperature prior to supply of the infusion fluid into a living body, a latent-heat-type heat accumulator member is disposed in the vicinity of the infusion fluid, and the infusion fluid is warmed by using a latent heat generated in phase change of the heat accumulator member from liquid phase to solid phase.

In this method, prior to the supply of the infusion fluid into the living body, the infusion fluid is warmed by using the latent heat generated in the phase change of the latent-heat-type heat accumulator member from the liquid phase to the solid phase. The latent-heat-type heat accumulator member rapidly generates the latent heat in the phase change, and a temperature of the generated heat can be rapidly elevated and then held substantially constant for a relatively large length of time, so that it is possible to rapidly warm the infusion fluid even in a circumstance without availability of a power source, and maintain the warmed infusion fluid at a constant temperature from an initial stage of the warming for a relatively large length of time.

The gist of an apparatus invention as a second invention for suitably carrying out the above-described first invention is that, in an infusion fluid warming apparatus for warming an infusion fluid to a predetermined temperature prior to supply of the infusion fluid into a living body through an infusion fluid tube, the apparatus includes (a) a tube holding device detachably holding the infusion fluid tube, and (b) a latent-heat-type heat accumulator member which is disposed in the tube holding device, and which warms the infusion fluid passing through the infusion fluid tube that is held by the tube holding device, by a latent heat generated in phase change of the heat accumulator member from liquid phase to solid phase.

In this apparatus, prior to the supply of the infusion fluid into the living body through the infusion fluid tube, the infusion fluid is warmed by using the latent heat generated in the phase change of the latent-heat-type heat accumulator member (which is disposed in the tube holding device holding the infusion fluid tube) from the liquid phase to the solid phase. The latent-heat-type heat accumulator member rapidly generates the latent heat in the phase change, and a temperature of the generated heat can be rapidly elevated and then held substantially constant for a relatively large length of time, thereby making it possible to rapidly warm the infusion fluid passing through the infusion fluid tube even in a circumstance without availability of a power source, and maintain the warmed infusion fluid at a constant temperature from an initial stage of the warming for a relatively large length of time.

It is preferable that the above-described latent-heat-type heat accumulator member is constituted by any one of paraffin-based heat accumulating material, salt-hydrate-based heat accumulating material and clathrate-hydrate-based heat accumulating material. Since any of the paraffin-based heat accumulating material, salt-hydrate-based heat accumulating material and clathrate-hydrate-based heat accumulating material generates the latent heat in the phase change from the liquid phase to the solid phase, it is possible to maintain the infusion fluid (passing through the infusion fluid tube) at a constant temperature from an initial stage of the warming for a relatively large length of time, by setting a melting point of the heat accumulator member in a temperature suitable for the infusion fluid, for example, about 36-50 degrees that is in the vicinity of a body temperature of the living body or is higher than the body temperature.

Further, it is preferable that the latent-heat-type heat accumulator member is constituted by a heat accumulating material having a characteristic that the material is placed in a supercooled state in which the material is held in the liquid phase even if the material is cooled from a melting-point. The heat accumulating material is changed from the liquid phase to the solid phase in response to stimulus applied to the material placed in the supercooled state, and emits the latent heat as a result of the phase change. In this arrangement, the latent-heat-type heat accumulator member does not generate the heat while being held in a reserving state that corresponds to the supercooled liquid phase state, and the temperature of the generated heat can be rapidly elevated in response to the stimulus, and then held substantially constant for a relatively large length of time, so that it is possible to maintain the warmed infusion fluid (passing through the infusion fluid tube) at a constant temperature from an initial stage of the warming for a relatively large length of time.

Further, it is preferable that the latent-heat-type heat accumulator member is constituted by the heat accumulating material, a trigger member which initiates the phase change of the heat accumulating material from the liquid phase to the solid phase in response to a heat generation initiating operation, and a flexible accommodating bag which fluid-tightly accommodates the heat accumulating material and the trigger member. In this arrangement, the heat accumulator member is stored in the form of the accommodating bag, and the trigger member initiates the phase change of the heat accumulating material (placed in the supercooled state) from the liquid phase to the solid phase, in response to the heat generation initiating operation, so that the temperature of the generated heat can be rapidly elevated at a desired timing and then held substantially constant for a relatively large length of time. It is therefore possible to maintain the warmed infusion fluid (passing through the infusion fluid tube) at a constant temperature from an initial stage of the warming for a relatively large length of time. Further, the warming of the infusion fluid (passing through the infusion fluid tube) is substantially continued even in replacement of the latent-heat-type heat accumulator member.

Further, it is preferable that the tube holding device has a tube holding member holding the infusion fluid tube in a predetermined curved shape, and the accommodating bag is detachably held in close contact directly or indirectly with the tube holding member. In this arrangement, since the latent-heat-type heat accumulator member taking the form of the accommodating bag is detachably held in the tube holding device, an operation for replacement of the latent-heat-type heat accumulator member is facilitated.

Further, it is preferable that the accommodating bag is constituted by a flexible sheet (including a metal layer or layers), and has a heat conducting fin. The heat conducting fin includes an end portion connected to a contact portion of the flexible sheet that is in close contact with the tube holding member, and another end portion separated from the contact portion of the flexible sheet. The heat accumulating material accommodated in the accommodating bag is phase-changed to the solid phase as a result of emission of the latent heat, wherein the phase change is initiated from the side of the above-described contact portion of the flexible sheet that is in close contact with the tube holding member. Thus, the latent heat emitted from a portion of the material held in the liquid phase is thermally conducted through a portion of the material placed in the solid phase, so that it is not possible to avoid sequential reduction in the temperature of the infusion fluid due to reduction in efficiency of the warming. However, in the above-described arrangement, the heat is conducted from the portion of the material held in the liquid phase, to the side of the contact portion of the flexible sheet, through the heat conducting fin, whereby the reduction in the temperature of the warmed infusion fluid can be advantageously restrained.

Further, it is preferable that the tube holding device has an electric heater for heating the latent-heat-type heat accumulator member so as to cause the phase change of the heat accumulator member from the solid phase to the liquid phase. This arrangement provides an advantage that the heat accumulator member can be repeatedly placed in a reusable state while being disposed in the tube holding device, where the heat accumulator member is heated to a temperature that is not lower than the melting point.

The gist of an infusion fluid warming bag as a third invention, which is suitably used in the method invention as the first invention and the apparatus invention as the second invention, is that, in an infusion fluid warming bag which is to be disposed in the vicinity of an infusion fluid, for warming the infusion fluid to a predetermined temperature prior to supply of the infusion fluid into a living body, there are included (a) a bag-shaped main body, and (b) a heat accumulating material which is accommodated in the bag-shaped main body and which generates a latent heat in phase change of the material from liquid phase to solid phase.

In this arrangement, the an infusion fluid warming bag, which is to be disposed in the vicinity of the infusion fluid, for warming the infusion fluid to the predetermined temperature prior to supply of the infusion fluid into the living body, is constructed to include the bag-shaped main body and the heat accumulating material which is accommodated in the bag-shaped main body and which generates the latent heat in the phase change of the material from the liquid phase to the solid phase. The latent-heat-type heat accumulator member accommodated in the infusion fluid warming bag rapidly generates the latent heat in the phase change from the liquid phase to the solid phase, and a temperature of the generated heat can be rapidly elevated and then held substantially constant for a relatively large length of time. Thus, by using the present infusion fluid warming bag so as to warm the infusion fluid, it is possible to rapidly warm the infusion even in a circumstance without availability of a power source, and maintain the warmed infusion fluid at a constant temperature from an initial stage of the warming for a relatively large length of time.

It is preferable that the bag-shaped main body has an outer bag constituted by a flexible sheet, and a heat conducting member including a portion held in contact with a warming surface of the flexible sheet that is to be opposed to the infusion fluid and another portion separated from the warming surface of the flexible sheet. The heat accumulating material accommodated in the accommodating bag is phase-changed to the solid phase as a result of emission of the latent heat, wherein the phase change is initiated from the side of the above-described warming surface of the flexible sheet that is in close contact with the tube holding member. Thus, the latent heat emitted from a portion of the material held in the liquid phase is thermally conducted through a portion of the material placed in the solid phase, so that it is not possible to avoid sequential reduction in the temperature of the infusion fluid due to reduction in efficiency of the warming. However, in the above-described arrangement, the heat is conducted from the portion of the material held in the liquid phase, to the side of the warming surface of the flexible sheet, through the heat conducting member, whereby the reduction in the temperature of the warmed infusion fluid can be advantageously restrained.

Further, it is preferable that the heat conducting member is provided by a plurality of heat conducting fins each including an end portion connected to the warming surface of the flexible sheet that is to be opposed to the infusion fluid and another end portion separated from the worming surface of the flexible sheet. In this arrangement, as described above, the heat is conducted from the portion of the material held in the liquid phase, to the side of the warming surface of the flexible sheet, through the heat conducting member, whereby the reduction in the temperature of the warmed infusion fluid can be advantageously restrained. Further, since each of the heat conducting fins has a thin-sheet-like shape, it is easily deformable as well as the outer bag.

Further, it is preferable that the flexible sheet constituting the outer bag is a composite sheet including metal and resin layers that are superposed on each other. In this arrangement in which a light is blocked by the metal layer or layers, the heat accumulating material accommodated in the outer bag is prevented from being deteriorated, whereby the heat accumulating material has an increased durability.

BEST MODE FOR CARRYING OUT THE INVENTION

Hereinafter, there will be described embodiments of the present invention, with reference to the drawings.

Figure 1:
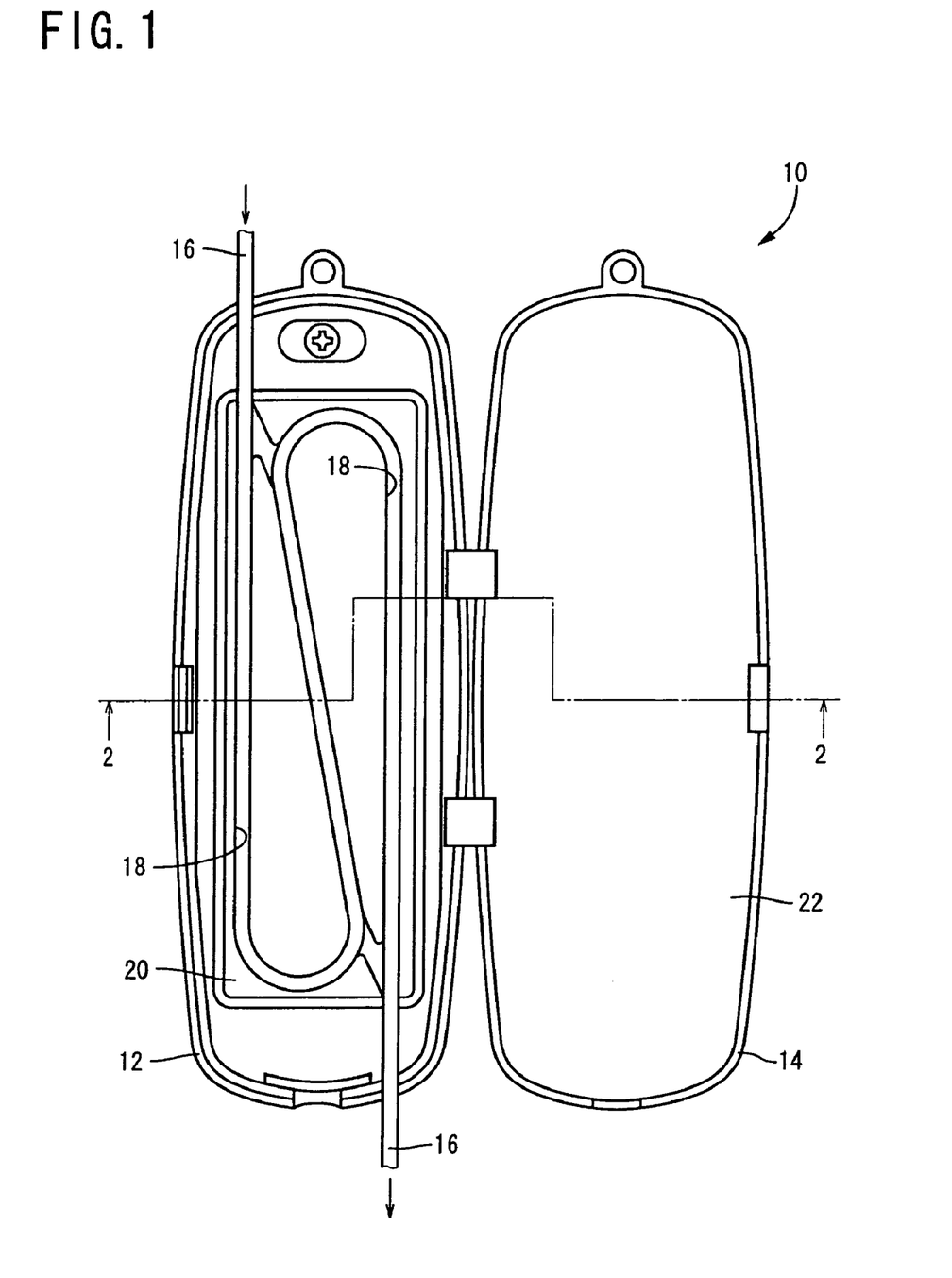
FIG. 1 is a front view for explaining construction of an infusion fluid warming apparatus as a first embodiment of the present invention, and showing a state in which an upper cover of the apparatus is open.
Figure 2:
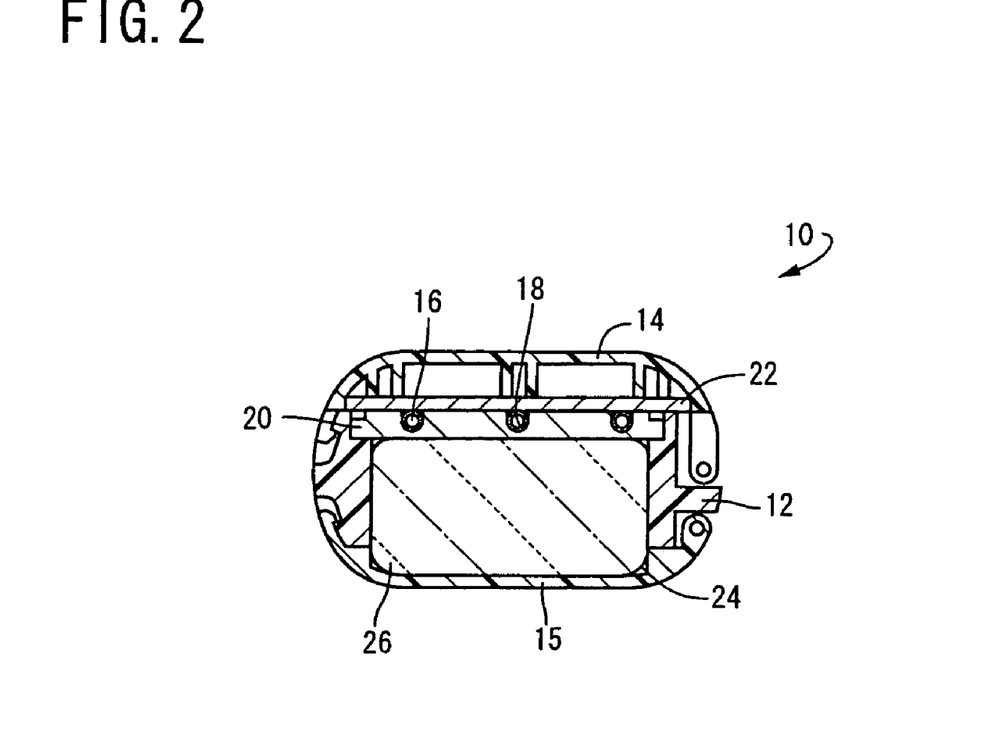
FIG. 2 is a cross sectional view taken along line 2-2 of FIG. 1, and showing a state in which the upper cover of the apparatus of FIG. 1 is closed.

FIGS. 1 and 2 are views for explaining construction of an infusion fluid warming apparatus 10 as an example to which the present invention is applied. FIG. 1 is a front view showing the infusion fluid warming apparatus 10 in a state in which a cover body 14 is open. FIG. 2 is a cross sectional view taken along line 2-2 of FIG. 1 and showing the infusion fluid warming apparatus 10 in a state in which the cover body 14 is closed.

As shown in FIGS. 1 and 2, the infusion fluid warming apparatus 10 has an elongated-shaped casing body 12, the upper cover 14 which is pivotably connected to a side portion of the casing body 12 and which opens and closes an upper surface (front surface) that is a surface of the casing body 12, and a lower cover 15 which is pivotably connected to the side portion of the casing body 12 and which opens and closes a lower surface (rear surface) that is another surface of the casing body 12. Each of the casing body 12 and upper and lower covers 14, 15 is constituted, for example, by a relatively hard plastic. In a surface of the casing body 12, there is fitted a tube holding plate 20 functioning as a tube holding member. The tube holding plate 20 has a groove 18 into which an infusion fluid tube 16 is to be fitted. The tube holding plate 20 is fixed to the casing body 12 by means of, for example, threaded screws. The groove 18 has a letter-U shaped bottom with a depth and a width that are substantially the same as an outer circumferential surface of the infusion fluid tube 16, so that the groove 18 is held in close contact with the infusion fluid tube 16. Further, for holding the infusion fluid tube 16 in a predetermined shape, the groove 18 has a letter S shape. The tube holding plate 20 is constituted by polypropylene resin or other material such as aluminum alloy which is better than the polypropylene resin with respect to heat conductivity.

A presser plate 22 is fixed inside the upper cover 14, so that the infusion fluid tube 16 disposed in the groove 18 is pressed by the presser plate 22 while the upper surface of the casing body 12 is closed by the upper cover 14. The infusion fluid tube 16 is thus sandwiched between the presser plate 22 and the tube holding plate 20, so as to be fixed. The groove 18 formed in the tube holding plate 20 includes two curved portions and a straight portion that connects the two curved portions. The straight portion is held in communication with entrance and exit of the groove 18, so that the infusion fluid tube 16 can be held by the infusion fluid warming apparatus 10 also while the tube 16 is fitted in only the straight portion. It is therefore possible to select, as a warming length of the infusion fluid tube 16, one of two cases, i.e., a case where the tube 16 is held in a letter-S shaped curve and a case where the tube 16 is held in a letter-I shaped curve. In the present embodiment, the casing body 12, the tube holding plate 20 (fitted in the casing body 12) and the upper and lower covers 14, 15 cooperate with each other to constitute a tube holding device for holding a part of the infusion fluid tube 16.

The casing body 12 defines therein a rectangular parallelepiped space 24 having a surface that is closed by the tube holding plate 20. In the space 24, an infusion fluid warming bag 26 is accommodated to function as a latent-heat-type heat accumulator member or a latent-heat-type warming member. The infusion fluid warming bag 26 is preferably held in close contact with a rear surface of the tube holding plate 20. In the infusion fluid warming bag 26, there is fluid-tightly accommodated a latent-heat-type heat accumulating material 28 such as paraffin-based heat accumulating material, salt-hydrate-based heat accumulating material and clathrate-hydrate-based heat accumulating material. The latent-heat-type heat accumulating material 28 generates a latent heat in its phase change from liquid phase to solid phase. It is common that the heat accumulating material 28 is accommodated while being impregnated in a sponge-like continuous porous member or a foamed sheet material, so that the heat accumulating material 28 does not flow to be unevenly distributed when being in the liquid phase.

As the above-described paraffin-based heat accumulating material, for example, $C_{14}$~$C_{16}$ paraffin, $C_{15}$~$C_{16}$ paraffin, L-decal, $C_{14}$ paraffin, $C_{16}$ paraffin or high-density polyethylene is used. As the above-described salt-hydrate-based heat accumulating material, for example, $CaCl_2.6H_2O$, $Na_2SO_4.10H_2O$, $Na_2CO_3.10H_2O$, $NaHPO_4.12H_2O$, $Ca(NO_3)_2.4H_2O$, $Na_2S_2O_3.5H_2O$, $NaCH_3COO.3H_2O$, $Ba(OH)_2.8H_2O$, $Sr(OH)_2.8H_2O$, $Mg(NO_3)_2.6H_2O$, $KAl(SO_4)_2.12H_2O$, $NH_4Al(SO_4)_2.12H_2O$, $MgCl_2.6H_2O$, $KNO_3$—$LiNO_3$ or $KNO_3$—$LiNO_3$—$NaNO_3$ is used. The salt-hydrate-based heat accumulating material is a compound crystal in which water molecule is combined with salt ($CaCl_2$). The salt-hydrate-based heat accumulating material is superior to the paraffin-based heat accumulating material in respect to heat of fusion and conductivity per unit volume, and somewhat exhibits a supercooling phenomenon. As the above-described clathrate-hydrate-based heat accumulating material, for example, $SO_2.6H_2O$ (under 1 atmosphere), $C_4H_8O.17H_2O$, $(CH_3)_3N.101/4H_2O$, $(C_4H_9)_4NCHO_2.32H_2O$ or $(C_4H_9)_4NCH_3CO_2.32H_2O$ is used. The clathrate-hydrate-based heat accumulating material is a compound in which water molecule takes the form of a three-dimensional network structure which is different from an ordinary ice and which contains other molecule (e.g., $C_4H_8O$) incorporated in a space formed therein. The clathrate-hydrate-based heat accumulating material exhibits the supercooling phenomenon. It is noted that the supercooling phenomenon is exhibited owing to a character by which the material is kept in the liquid phase without initiation of solidification even when the material is cooled to a temperature lower than the melting point.

The heat accumulating material 28 has a relatively large heat accumulating capacity. Further, the heat accumulating material 28 has the melting point of the material 28 that can be set at a desired degree, and a character by which phase separation is restrained. Among the examples specified as the heat accumulating material 28, acetic-acid soda ($NaCH_3COO.3H_2O$) and sodium sulfate ($Na_2SO_4.10H_2O$: Glauber's salt) are particularly excellent with respect to a large heat accumulating capacity. The melting temperature of the acetic-acid soda can be set at a desired value within a range from 31.5° to 58.4°, for example, by adding a certain ratio of urea to the acetic-acid soda. Moreover, the phase separation of the acetic-acid soda can be remarkably prevented by mixing thereto 0.5-5 wt % of xanthan gum or by mixing thereto a mixture of 0.5-5 wt % of xanthan gum, locust bean gum and guar gum.

Figure 3:
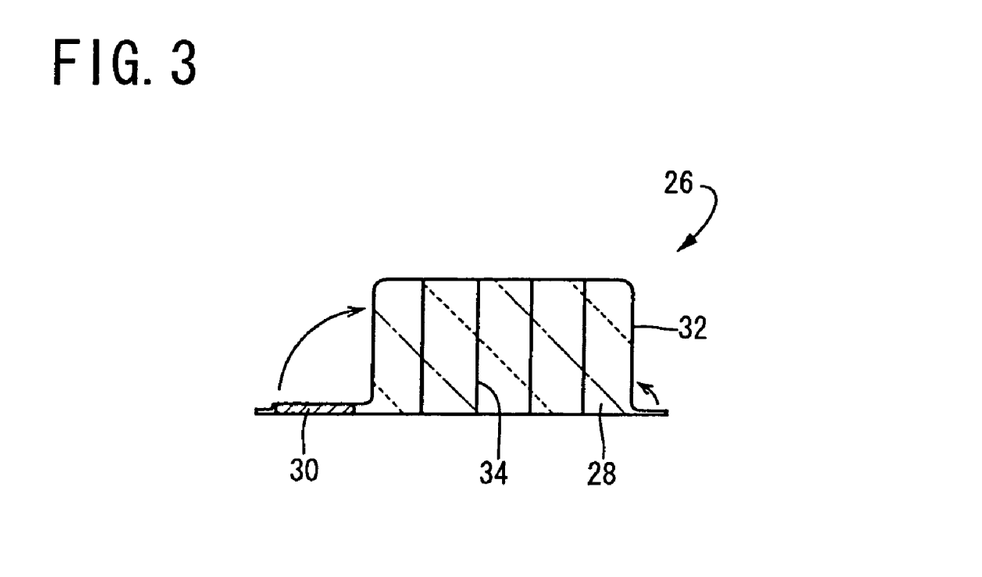
FIG. 3 is a cross sectional view for explaining construction of an infusion fluid warming bag disposed in the apparatus of FIG. 1.

It is preferable that, in the infusion fluid warming bag 26, there is accommodated, for example, either one of the above-described salt-hydrate-based heat accumulating material and clathrate-hydrate-based heat accumulating material, as the latent-heat-type heat accumulating material 28 which is held in the liquid phase even if the material 28 is cooled from the melting point and which is changed from the liquid phase to the solid phase in response to stimulus applied to the material 28 placed in the supercooled state. As shown in a cross sectional view of FIG. 3 in detail, the infusion fluid warming bag 26 is constituted by the heat accumulating material 28, a trigger member 30 which initiates the phase change of the heat accumulating material 28 from the liquid phase to the solid phase in response to a heat generation initiating operation, and an outer bag (accommodating bag) 32 which accommodates the heat accumulating material 28 and the trigger member 30 in a fluid-tight state. As shown in the cross sectional view of FIG. 3 in detail, the accommodating bag 32 is constituted by a flexible sheet as a composite material including a metal layer (such as aluminum) and a resin layer that are superposed on each other, and has a plurality of heat conducting fins 34 each including an end portion and another end portion. The end portion of each heat conducting fin 34 is connected to an upper surface portion (as seen in FIG. 3) of the flexible sheet, i.e., a surface portion of the flexible sheet that is in close contact with the tube holding plate 20, while the other end portion of each heat conducting fin 34 is separated from the close contact surface portion of the flexible sheet and is connected to the opposite side portion of the flexible sheet. Each heat conducting fin 34 is preferably constituted by a metallic foil such as aluminum foil which has high degrees of heat conductivity and flexibility.

The trigger member 30 is constituted by a metal disc made of stainless steel and magnetic iron steel, and is subjected to a mechanical deformation given by an external operation at a desired point of time, so as to be caused to positively generate a metal ion, thereby causing the phase change of the heat accumulating material 28 (placed in the supercooled state) from the liquid phase to the solid phase, and causing the heat accumulating material 28 to emit the latent heat in process of the phase change.

Figure 4:
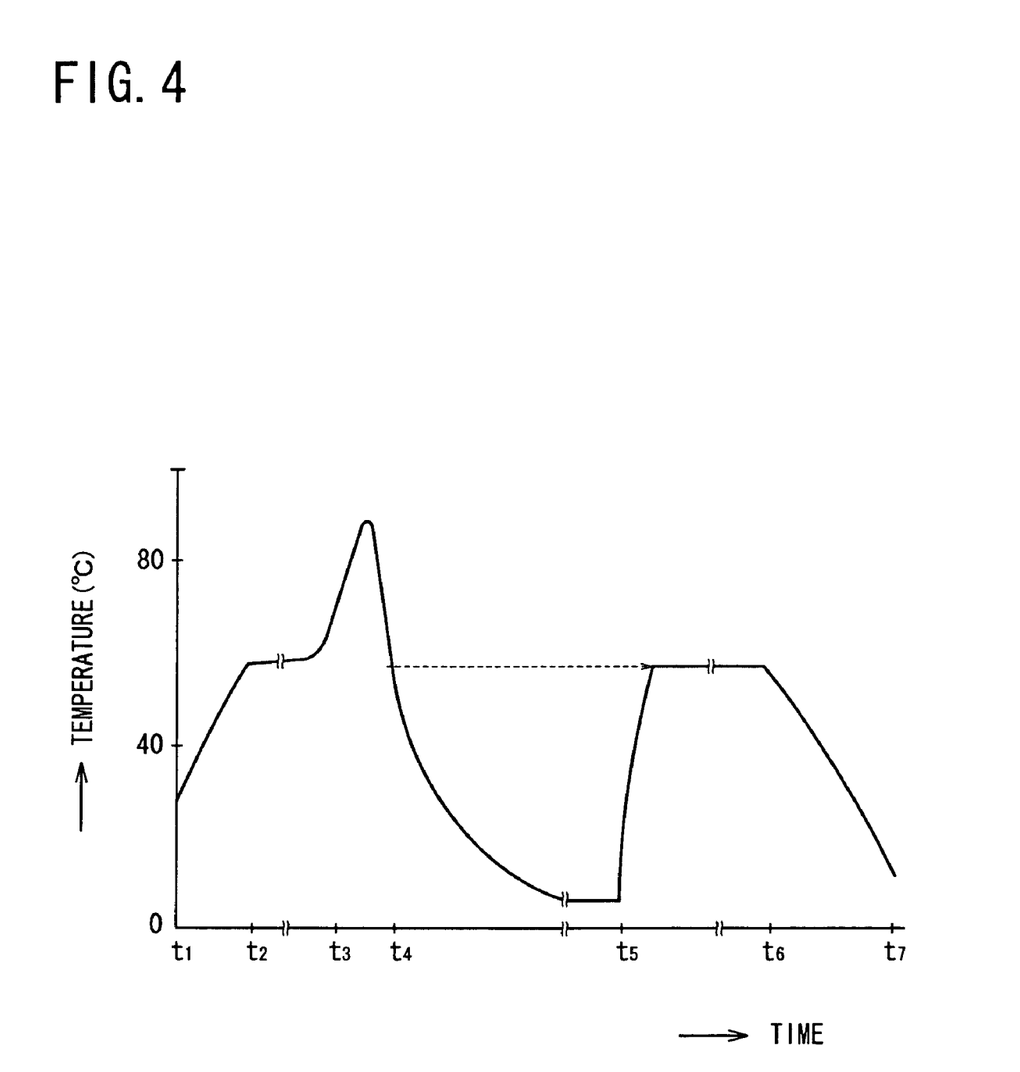
FIG. 4 is a view for explaining a temperature characteristic of a latent-heat-type heat accumulating material accommodated in the infusion fluid warming bag disposed in the apparatus FIG. 1.

FIG. 4 is a view for explaining a characteristic of the latent-heat-type heat accumulating material 28. As shown in the view, when the temperature of the heat accumulating material 28 is elevated to the vicinity of a melting point by warming the material 28 (placed in the solid phase) by a warm bath or an electric heater, the phase change of the material 28 to the liquid phase takes place (at a point $t_1$ of time). After that, a heat is accumulated. In this period of the heat accumulation (from a point $t_2$ of time to a point $t_3$ of time), the temperature is held substantially constant. When the heat accumulation has been finished upon stopping of the warming of the material 28, the temperature of the material 28 is once elevated. After having been once elevated, the temperature of the material 28 is gradually lowered by self-cooling and eventually lowered to an ordinary temperature that is lower than the melting point, while the material 28 is held in the liquid phase. Thus, the material 28 is placed in the liquid phase of the supercooled state. Then, when the trigger member 30 is deformed as a result of the heat generation initiating operation, the phase change of the material 28 (placed in the supercooled state) to the solid phase is initiated in response to the deformation of the trigger member 30 (at a point $t_5$ of time). After having been elevated to the vicinity of the melting point, the temperature of the material 28 is held constant in the vicinity of the melting point for a relatively large length of time (from point $t_5$ of time to point $t_6$ of time). Then, when the phase change to the solid phase is completed, the temperature of the material 28 is gradually lowered (point $t_7$ of time). It is noted that a latent-heat-type heat accumulating material without the supercooling phenomenon is held constant in the vicinity of the melting point from the point $t_4$ of time as indicated by broken line in FIG. 4.

In the infusion fluid warming apparatus 10 constructed as described above, prior to supply of the infusion fluid into a living body, the infusion fluid warming bag (latent-heat-type heat accumulator member) 26 disposed in the vicinity of the infusion fluid in the infusion fluid tube 16 generates the latent heat generated in the phase change from the liquid phase to the solid phase, whereby the infusion fluid in the infusion fluid tube 16 is warmed by the latent heat. The infusion fluid warming bag (latent-heat-type heat accumulator member) 26 is held in close contact with the rear surface of the tube holding plate 20, so as to be disposed in the vicinity of the infusion fluid, i.e., in such a position relative to the infusion fluid tube 16 (held between the upper cover 14 and the tube holding plate 20 fitted in the casing body 12 constituting the tube holding device) that enables the infusion fluid to be warmed. The thus disposed infusion fluid warming bag 26 generates the latent heat generated in the phase change from the liquid phase to the solid phase, whereby the infusion fluid in the infusion fluid tube 16 is warmed by the latent heat. The latent-heat-type heat accumulating material 28 disposed in the infusion fluid warming bag (latent-heat-type heat accumulator member) 26 rapidly generates the latent heat in the phase change from the liquid phase to the solid phase, and the temperature of the generated heat can be rapidly elevated and then held substantially constant for a relatively large length of time, so that it is possible to rapidly warm the infusion fluid passing through the infusion fluid tube 16 even in a circumstance without availability of a power source, and maintain the warmed infusion fluid at a constant temperature from an initial stage of the warming for a relatively large length of time.

Further, in the present embodiment, the infusion fluid warming bag (latent-heat-type heat accumulator member) 26 is constituted by any one of paraffin-based heat accumulating material, salt-hydrate-based heat accumulating material and clathrate-hydrate-based heat accumulating material. Since any of the paraffin-based heat accumulating material, salt-hydrate-based heat accumulating material and clathrate-hydrate-based heat accumulating material generates the latent heat in the phase change from the liquid phase to the solid phase, it is possible to maintain the infusion fluid (passing through the infusion fluid tube 16) at a constant temperature from an initial stage of the warming for a relatively large length of time, by setting a melting point of the heat accumulator member in a temperature suitable for the infusion fluid, for example, about 36-50 degrees that is in the vicinity of a body temperature of the living body or is higher than the body temperature.

Further, in the present embodiment, the infusion fluid warming bag (latent-heat-type heat accumulator member) 26 is constituted by the heat accumulating material 28 which is placed in the supercooled state in which the material 28 is held in the liquid phase even if it is cooled from the melting point. The heat accumulating material 28 is changed from the liquid phase to the solid phase in response to stimulus applied to the material 28 placed in the supercooled state, and emits the latent heat as a result of the phase change. In this arrangement, the infusion fluid warming bag (latent-heat-type heat accumulator member) 26 does not generate the heat while being held in a reserving state, and the temperature of the generated heat can be rapidly elevated in response to the stimulus and then held substantially constant for a relatively large length of time, so that it is possible to maintain the warmed infusion fluid (passing through the infusion fluid tube 16) at a constant temperature from an initial stage of the warming for a relatively large length of time.

Further, in the present embodiment, the infusion fluid warming bag (latent-heat-type heat accumulator member) 26 is constituted by the heat accumulating material 28, the trigger member 30 which initiates the phase change of the heat accumulating material 28 from the liquid phase to the solid phase in response to the heat generation initiating operation, and the flexible accommodating bag 32 which fluid-tightly accommodates the heat accumulating material 28 and the trigger member 30. In this arrangement, the heat accumulator member 28 is stored in the form of the accommodating bag 32, and the trigger member 30 initiates the phase change of the heat accumulating material 28 (placed in the supercooled state) from the liquid phase to the solid phase, in response to the heat generation initiating operation, so that the temperature of the generated heat can be rapidly elevated at a desired timing and then held substantially constant for a relatively large length of time. It is therefore possible to maintain the warmed infusion fluid (passing through the infusion fluid tube 16) at a constant temperature from an initial stage of the warming for a relatively large length of time. Further, the warming of the infusion fluid (passing through the infusion fluid tube 16) is substantially continued even in replacement of the infusion fluid warming bag (latent-heat-type heat accumulator member) 26.

Further, in the present embodiment, the tube holding device including the casing body 12 and the upper cover 14 has the tube holding plate (tube holding member) 20 holding the infusion fluid tube 16 in the predetermined curved shape, and the accommodating bag 32 is detachably held in close contact directly or indirectly with the tube holding member 16, by opening and closing the lower cover 15. Since the infusion fluid warming bag (latent-heat-type heat accumulator member) 26 taking the form of the bag is detachably held in the tube holding device, an operation for replacement of the latent-heat-type heat accumulator member is facilitated.

Further, in the present embodiment, the accommodating bag 32 constituting the infusion fluid warming bag 26 is constituted by the flexible sheet including the metal layer or layers, and has the heat conducting fins 34. Each of the heat conducting fins 34 includes the end portion connected to the contact portion of the flexible sheet that is in close contact with the tube holding member 20, and another end portion separated from the contact portion of the flexible sheet. The heat accumulating material 28 accommodated in the accommodating bag 32 is phase-changed to the solid phase as a result of emission of the latent heat, wherein the phase change is initiated from the side of the above-described contact portion of the flexible sheet. Thus, the latent heat emitted from a portion of the material 28 held in the liquid phase is thermally conducted through a portion of the material 28 placed in the solid phase, so that it is not possible to avoid sequential reduction in the temperature of the infusion fluid due to reduction in efficiency of the warming. However, in the above-described arrangement, the heat is conducted from the portion of the material held in the liquid phase, to the side of the contact portion of the flexible sheet, through the heat conducting fins 34, whereby the reduction in the temperature of the warmed infusion fluid can be advantageously restrained.

There will be next described another embodiment of the present invention. In the following description, the same reference signs as used in the above-described embodiment will be used to identify the functionally corresponding elements, and the descriptions thereof will not be provided.

Figure 5:
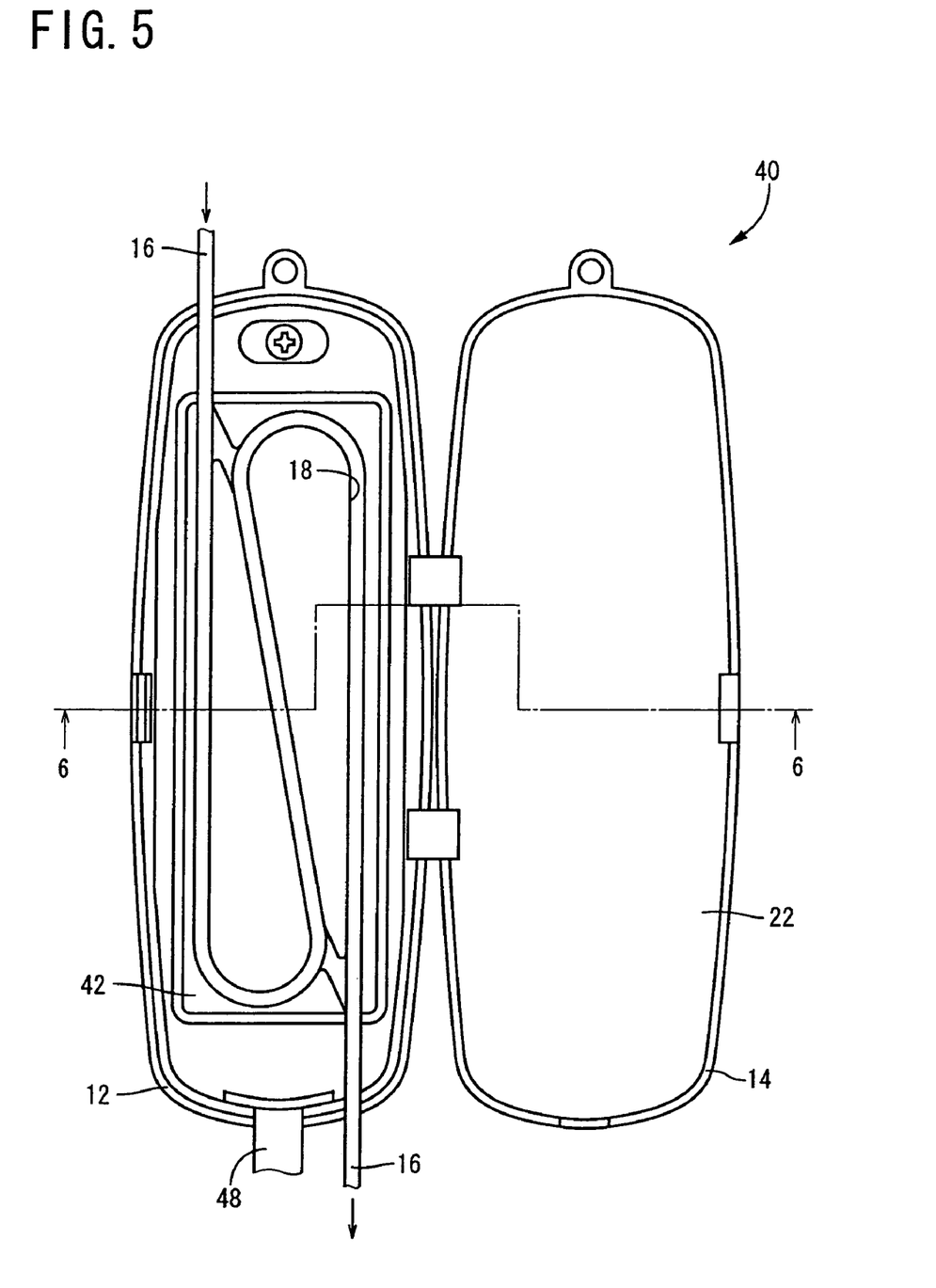
FIG. 5 is a front view corresponding to the view of FIG. 1, and explaining construction of an infusion fluid warming apparatus as another embodiment of the present invention.
Figure 6:
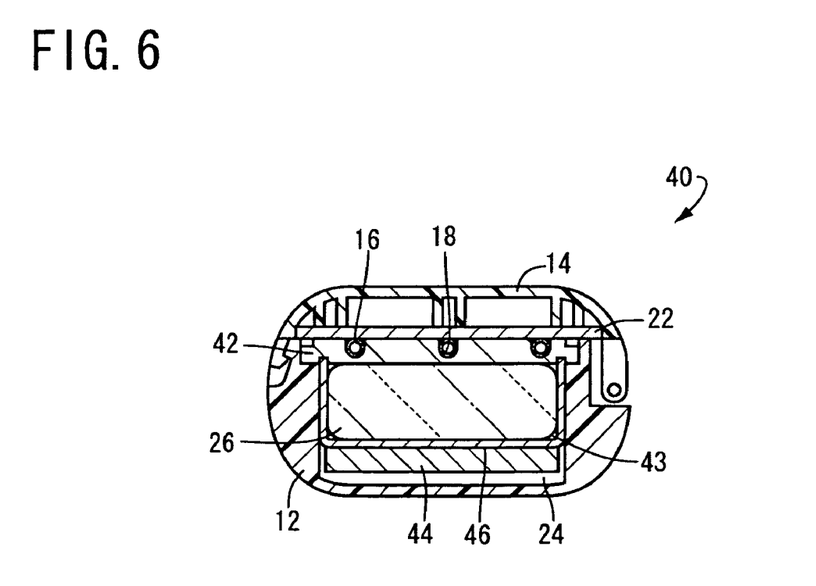
FIG. 6 is a cross sectional view corresponding to the view of FIG. 2, taken along line 6-6 of FIG. 5, and showing a state in which an upper cover of the apparatus of FIG. 5 is closed.
Figure 7:
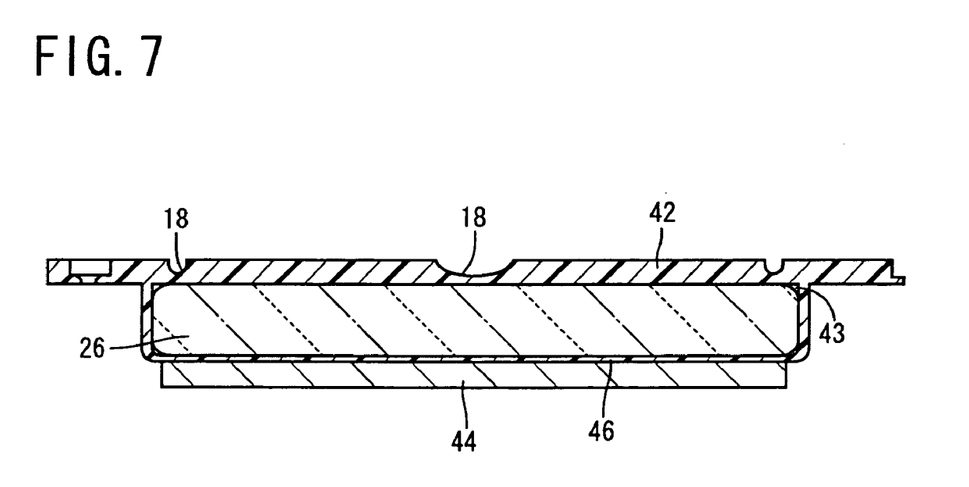
FIG. 7 is a longitudinal cross sectional view for explaining construction of a tube holding plate of FIG. 6.

FIG. 5 is a front view showing a state in which the upper cover 14 is open in an infusion fluid warming apparatus 40 as another embodiment of the present invention. FIG. 6 is a cross sectional view showing a state in which the upper cover is closed in the infusion fluid warming apparatus 40 of FIG. 5. FIG. 7 is a longitudinal cross sectional view showing a tube holding plate 42 that is fitted in the infusion fluid warming apparatus 40.

The infusion fluid warming apparatus 40 of the present embodiment has the tube holding plate 42 fitted in an upper opening of the casing body 12. A front surface (upper surface) of the tube holding plate 42 is constructed substantially the same as that of the above-described tube holding plate 20. However, on the side of a rear surface (lower surface) of the tube holding plate 42, an accommodating space 43 is formed to accommodate the infusion fluid warming bag 26 containing the heat accumulating material 28, and a bracket 46 is provided to be spaced apart from the rear surface of the tube holding plate 42 by a constant distance. An electric heater 44 is fixed to the bracket 46. The infusion fluid warming bag 26 is fitted between the bracket 46 and the rear surface of the tube holding plate 42, and is held in close contact with the bracket 46 and the rear surface of the tube holding plate 42. In FIG. 5, a reference sign 48 denotes a power supply cable connected to the electric heater 44. It is preferable to use, as the electric heater 44, a ceramic heater equipped with a function of maintaining a predetermined heat temperature independently of an outside air temperature or an ambient temperature.

In the infusion fluid warming apparatus 40 of the present embodiment, since the heat accumulating material 28 accommodated in the infusion fluid warming bag 26 is heated by the electric heater 44 to a temperature that is not lower than the melting point, there is an advantage that the heat accumulating material 28 is warmed to accumulate the heat in process of the phase change from the solid phase to the liquid phase while the infusion fluid warming bag 26 is being disposed in the casing body 12, after the heat accumulating material 28 has emitted the latent heat based on the phase change from the liquid phase to the solid phase. Therefore, where the heat accumulating material 28 is the paraffin-based heat accumulating material, the infusion fluid is continuously warmed by periodically warming the heat accumulating material 28 by the electric heater 44. That is, with use of a temperature adjusting device causing the electric heater 44 to warm the infusion fluid in the vicinity of the melting point, the heat accumulation by the heat accumulating material 28 as the paraffin-based heat accumulating material and the warming of the infusion fluid in the infusion fluid tube 16 by the electric heater 44 are performed concurrently with each other, while the infusion fluid is being warmed by the electric heater 44. The infusion fluid in the infusion fluid tube 16 is warmed by the latent heat emitted based on the phase change of the heat accumulating material 28 from the liquid phase to the solid phase, while the warming of the infusion fluid by the electric heater 44 is being suspended.

While the preferred embodiments of the present invention have been described in detail by reference to the drawings, it is to be understood that the invention is not limited to the details of the illustrated embodiments, but may be otherwise embodied.

For example, in the above-described embodiments, the infusion fluid in the infusion fluid tube 16 is warmed by the infusion fluid warming bag 26. However, the infusion fluid warming bag 26 may be held in close contact with an infusion fluid pack or infusion fluid storage bag, so that the infusion fluid stored in the infusion fluid storage bag can be warmed by the infusion fluid warming bag 26. In this arrangement, too, the warmed infusion fluid can be maintained by the infusion fluid warming bag 26 at a substantially constant temperature from an initial stage of the warming for a relatively large length of time.

Further, in the above-described embodiments, the infusion fluid warming bag 26 is provided by a bag whose shape is deformable to correspond to the shape of the space 24 or space 43. However, the infusion fluid warming bag 26 may be folded to be accommodated in the space 24 or space 43.

Further, in the above-described embodiments, the infusion fluid warming bag 26 is disposed to be held in close contact with the rear surface of the tube holding plate 20, 42. However, the infusion fluid warming bag 26 may be arranged to be held in close contact with the infusion fluid tube 16.

Further, in the above-described embodiments, the tube holding device constituted by elements such as the casing body 12 and the upper cover 14. However, the tube holding device may be formed in a cylindrical shape of a soft plastic, so that the cylindrical-shaped tube holding device includes a portion that can be opened and closed.

Further, in the above-described embodiments, the infusion fluid warmed by the infusion fluid warming bag 26 is not necessarily blood, plasma, physiological saline, nutrition fluid or medical fluid, but may be liquid nutrition food or the like. Where the infusion fluid is blood, plasma, physiological saline, nutrition fluid for injection or medical fluid for injection, for example, the infusion fluid is infused into a blood vessel of the living body through an intravenous drip cylinder, a roller clamp, an infusion fluid tube and a hypodermic needle that are connected to an infusion fluid container. Where the infusion fluid is oral nutrition fluid, oral medical fluid or liquid nutrition food, for example, the infusion fluid is supplied directly into a digestive organ of the living body through the infusion fluid tube connected to the infusion fluid container, or is supplied orally into a mouth of the living body through the infusion fluid tube.

The present invention can be carried out with various modifications within a range that is not deviated from the gist of the invention, although each of the possible modifications is not described.

The invention claimed is:

1. An infusion fluid warming apparatus for warming an infusion fluid to a predetermined temperature prior to supply of the infusion fluid into a living body through an infusion fluid tube, said apparatus comprising:
   a tube holding device detachably holding the infusion fluid tube; and
   a heat accumulator member generating a latent heat in phase change thereof from liquid phase to solid phase, said heat accumulator member being disposed in said tube holding device, so as to warm the infusion fluid passing through the infusion fluid tube that is held by said tube holding device, by the latent heat generated in the phase change from the liquid phase to the solid phase,
   wherein the latent-heat-type heat accumulator member is constituted by a heat accumulating material, a trigger member which initiates the phase change of the heat accumulating material from the liquid phase to the solid phase in response to a heat generation initiating operation, and a flexible accommodating bag which fluid-tightly accommodates the heat accumulating material and the trigger member,
   the flexible accommodating bag has an outer bag constituted by a flexible sheet, and a heat conducting member including a portion held in contact with a warming surface of the flexible sheet that is to be opposed to the infusion fluid and another portion separated from the warming surface of the flexible sheet, and
   the heat conducting member is provided by a plurality of flexible heat conducting fins each including an end portion connected to the warming surface of the flexible sheet that is to be opposed to the infusion fluid and another end portion separated from the warming surface of the flexible sheet.

2. The infusion fluid warming apparatus according to claim 1, where said heat accumulator member includes one of paraffin-based heat accumulating material, salt-hydrate-based heat accumulating material and clathrate-hydrate-based heat accumulating material.

3. The infusion fluid warming apparatus according to claim 1, wherein said heat accumulator member includes a heat accumulating material which is held in the liquid phase even at a temperature lower than a melting point of said heat accumulating material and which is changed from the liquid phase to the solid phase in response to stimulus applied to said heat accumulating material.

4. The infusion fluid warming apparatus according to claim 1,
wherein said tube holding device has a tube holding member holding the infusion fluid tube in a curved shape,
and wherein said accommodating bag is detachably held in contact with said tube holding member.

5. The infusion fluid warming apparatus according to claim 4,
wherein said accommodating bag is provided by a flexible sheet,
and wherein said accommodating bag has a heat conducting fin including an end portion connected to a contact portion of said flexible sheet that is in contact with said tube holding member, and another end portion separated from said contact portion of said flexible sheet.

6. The infusion fluid warming apparatus according to claim 1, wherein said tube holding device has an electric heater operable to heat said heat accumulator member so as to cause the phase change of said heat accumulator member from the solid phase to the liquid phase.

7. An infusion fluid warming bag which is to be disposed in the vicinity of an infusion fluid, for warming the infusion fluid to a predetermined temperature prior to supply of the infusion fluid into a living body, said infusion fluid warming bag comprising:
a bag-shaped main body; and
a heat accumulating material which is accommodated in said bag-shaped main body and which generates a latent heat in phase change thereof from liquid phase to solid phase,
wherein the bag-shaped main body has an outer bag constituted by a flexible sheet, and a heat conducting member including a portion held in contact with a warming surface of the flexible sheet that is to be opposed to the infusion fluid and another portion separated from the warming surface of the flexible sheet, and
the heat conducting member is provided by a plurality of flexible heat conducting fins each including an end portion connected to the warming surface of the flexible sheet that is to be opposed to the infusion fluid and another end portion separated from the warming surface of the flexible sheet.

8. The infusion fluid warming bag according to claim 7, wherein said flexible sheet is a composite sheet including metal and resin layers that are superposed on each other.

* * * * *